United States Patent [19]

Osther

[11] Patent Number: 5,516,895
[45] Date of Patent: May 14, 1996

[54] ANTIBODIES SPECIFIC TOWARDS GP 48

[75] Inventor: Kurt B. Osther, Scottsdale, Ariz.

[73] Assignee: Verigen, Inc., Hopkinton, Mass.

[21] Appl. No.: 195,617

[22] Filed: Feb. 14, 1994

Related U.S. Application Data

[62] Division of Ser. No. 772,604, Oct. 8, 1991, Pat. No. 5,286,852, which is a continuation of Ser. No. 376,247, Jul. 6, 1989, abandoned, which is a continuation-in-part of Ser. No. 215,867, Jul. 6, 1988, abandoned.

[51] Int. Cl.$^6$ .............................. C12P 21/08; C07K 16/10
[52] U.S. Cl. .................................. 530/388.35; 530/387.3; 530/389.4
[58] Field of Search ............................ 435/240.27, 252.3; 530/387.3, 388.35, 389.4

[56] References Cited

U.S. PATENT DOCUMENTS

| | | | |
|---|---|---|---|
| 4,132,769 | 1/1979 | Osther | 424/1.1 |
| 4,520,113 | 5/1985 | Gallo et al. | 435/5 |
| 4,722,888 | 2/1988 | Broder et al. | 435/5 |
| 5,286,852 | 2/1994 | Osther | 530/388.35 |

FOREIGN PATENT DOCUMENTS 8404327  4/1984  WIPO.

OTHER PUBLICATIONS

Thouvenot et al., Appl. Environ. Microb. 45:16–23 (1983).
Buchegger, F. et al., JNCI 79:337–342 (1987).
Pan et al., Journal of Infectous diseases 1987 155(4) p. 626.
Academic Press 1986. Goding *Monoclonal Antibodies: Principles and Practice*.

*Primary Examiner*—Lila Feisee
*Attorney, Agent, or Firm*—Banner & Allegretti, Ltd.

[57] ABSTRACT

Monoclonal and polyclonal antibodies specific towards, gp 48, having a molecular weight ranging from 46 kDa to 53 kDa. The gp 48 antibodies bind to the CD4 receptors on T4 lymphocytes, inhibiting if not neutralizing the HIV-1 virus from reacting therewith. Anti-gp 48 can be used for treating and diagnosing AIDS and related diseases.

1 Claim, 3 Drawing Sheets

ANTIBODIES SPECIFIC TOWARDS GP 48

RELATED APPLICATION

This application is a divisional from application Ser. No. 07/772,604, filed Oct. 8, 1991, and issued as U.S. Pat. No. 5,286,852, on Feb. 15, 1994; which was a continuation of application Ser. No. 07/376,247, filed Jul. 6, 1989, now abandoned; which was a continuation in part of application Ser. No. 07/215,867, filed Jul. 6, 1988, now abandoned.

BACKGROUND OF THE INVENTION

Acquired immune deficiency syndrome (AIDS) is recognized as an epidemic in several areas of the world, including the United States. The Human Immunodeficiency Virus (HIV-1), a retrovirus, has been identified as an etiologic cause of the disease. HIV-1 was previously identified as Human T-Cell Lymphotropic Virus Type III (HTLV-III) and Lymphadenopathy Associated Virus (LAV). The groups at highest risk of infection with HIV-1 include homosexual and bisexual men and abusers of injected drugs. Other predictable high-risk groups are women artificially inseminated with sperm from infected donors and sexual partners of those in the AIDS risk groups. Recipients of blood transfusions, blood products or organs are also at risk of contracting AIDS. There is also evidence that HIV-1 is transmitted heterosexually as a result of sexual contact.

Known therapies are generally limited to regimens designed to treat the opportunistic infections and neoplasias associated with AIDS and its related illnesses. Very few treatments are available, however, which attack the HIV-1 virus, the underlying cause of this often fatal disease. Among the known antiviral drugs, which are believed to merely slow down viral replication and which do not cure the disease, much less prevent reinfection, are azidothymidine (AZT), alpha interferon, gamma interferon, azimexon and isopinosine. Remission of some Kaposi sarcomas has been reported following treatment with alpha interferon, but the other antiviral drugs have not proven effective against HIV-1 infections. Immunomodulators, such as cimetidine and interleukin-2, which are intended to stimulate natural killer cell activity, and indomethacin, an antiinflammatory and prostaglandin inhibitor, have also been reported as useful in the treatment of AIDS. Present methods of treating individuals already infected with HIV-1 are scarce and largely ineffective.

SUMMARY OF THE INVENTION

The present invention is based upon the discovery of a protein characterized by binding in the 46,000 daltons to 53,000 daltons range upon resolution of HIV-1 infected cells having CD4 receptors in a Western Blot Assay (hereinafter gp 48). The invention relates to polyclonal and monoclonal antibodies specific towards gp 48 and methods of preventing and treating AIDS and related diseases.

The antibodies specific towards gp 48 (anti-gp 48) are capable of inhibiting HIV-1 infection of cells having CD4 receptors. The anti-gp 48 antibodies are characterized by their ability to bind in the gp 48 region of an immunoblot of solubilized HIV-1 infected cell proteins, wherein said cells have CD4 receptors. Further, the anti-gp 48 of the present invention inhibit binding in the gp 41, gp 120, and gp 160 regions of an immunoblot of solubilized HIV-1 infected cells, wherein the cells have CD4 receptors. The preferred gp 48 antibodies are porcine antibodies and more preferably monoclonal porcine antibodies.

The anti-gp 48 of the present invention can be used in immunotherapeutic methods of treating AIDS and related diseases and also in diagnostic methods or kits for detecting the presence or absence of viral particles responsible for AIDS or related diseases in biological samples. The present invention also encompasses the hybridomas which produce the monoclonal gp 48 antibodies, preferably porcine hybridomas, antibodies specific towards anti-gp 48 (anti-idiotype gp 48 antibodies), methods for producing the same, and vaccines comprising antiidiotype gp 48 antibodies or purified gp 48 protein.

DETAILED DESCRIPTION

Figure 1:
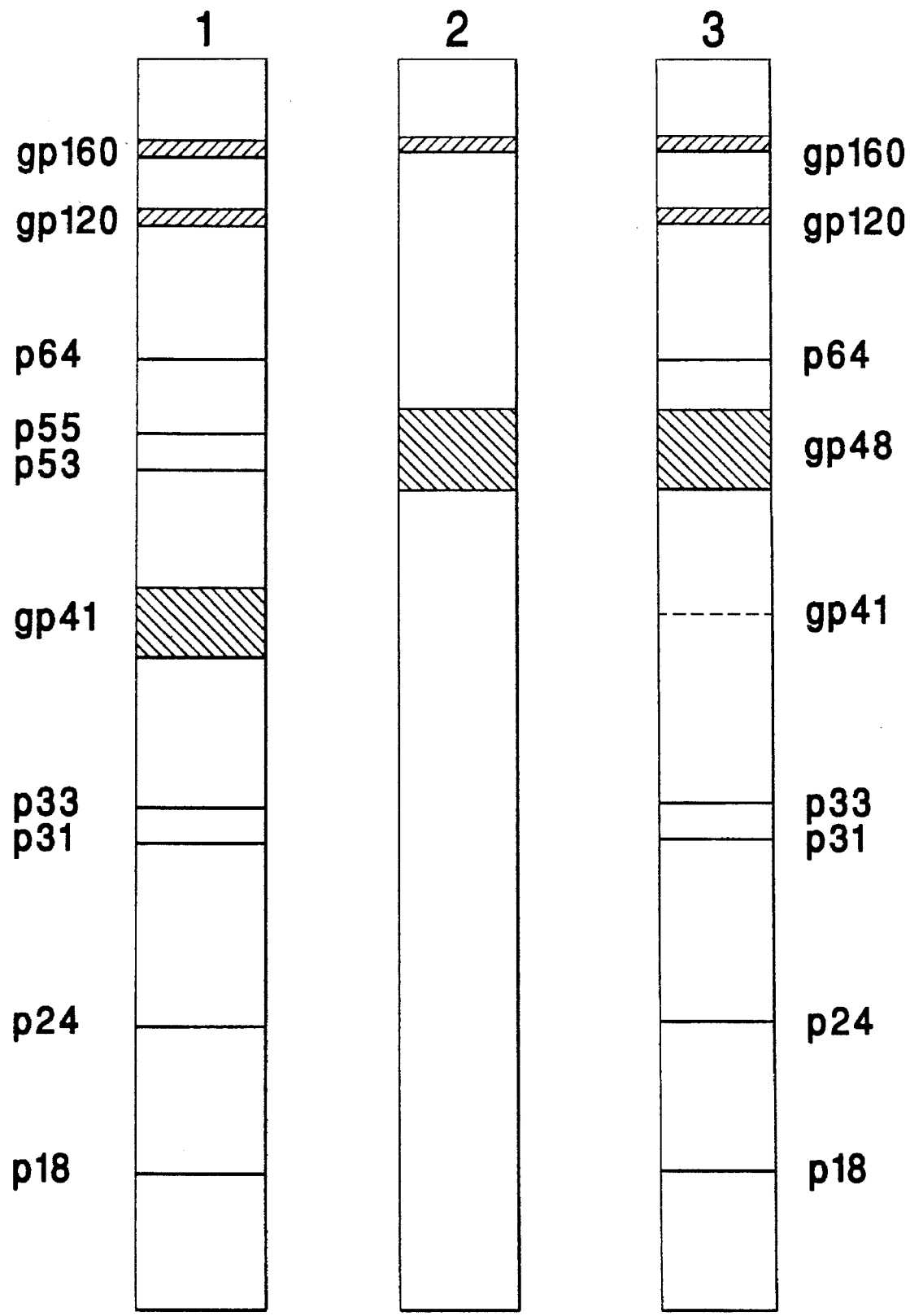
FIG. 1 is a drawing showing the protein banding produced by three of the sera tested in Examples 1–3 below, illustrating the presence of anti-gp 48 in each such serum.

The present invention relates to polyclonal and monoclonal antibodies useful in both the prevention and therapeutic treatment of AIDS and related diseases, methods of producing such antibodies, and such treatments per se. In particular, highly purified, solubilized HIV-1 virus preparations are resolved by Western Blot assay and a novel protein band having a molecular weight ranging from 46,000 Daltons to about 53,000 Daltons (the "gp 48" protein herein) is detected. It has been found that antibodies to the gp 48 protein (anti-gp 48) inhibit the binding of the HIV-1 virus to T4 lymphocytes. Anti-gp 48 as used herein is intended to encompass both polyclonal and monoclonal antibodies specific for the protein gp 48 and fragments thereof. Fragments of antibodies which would be useful within the present invention are those fragments capable or sufficient for binding of the antibody or fragment to gp 48 to occur.

The genomic origins of many of the HIV-1 specific antigens have previously been established (Essex, M., et al., *Ann. Int. Med.*, 103:700, 1985; Pan, L.-Z., et al., *J. Infect. Dis.*, 155:626, 1987; Lelie, P. N., et al *Lancet* 1:632 1987; Stute, R *Lancet*, 1:566, 1987; Veronese, F. D., et al., *Science*, 231:1289, 1987). The gag gene codes for a protein having a molecular weight of 55,000 Daltons (55 kDa), which can be cleaved into smaller proteins such as p24 (middle part of core) and p18, also named p17 (aminoterminus). The env gene encodes 90 kDa protein richly glycosylated to yield a 160 kDa glycoprotein (gp 160), which can be cleaved into a 120 kDa glycoprotein (gp 120), the amino-terminus of the external viral membrane; and a 41 kDa glycoprotein (gp 41), the carboxy-terminus transmembrane. Additionally, both the 64 kDa (p 64) and the 53 kDa (p 53) proteins have been shown to be related to reverse transcriptase. These proteins are related to the pol gene. Western Blot systems are capable of detecting antibodies to all the protein bands described above except for the 90 kDa protein.

Klatzmann, et al. first showed that HIV-1 selectively replicates in T4+ (CD4+) lymphocytes (Klatzmann, D., et al. *Nature*, 312:763, 1984). CD4+ is an essential component of the receptor for HIV-1 envelope protein gp 120. After binding to the target cell, HIV-1 enters the cell and is uncoated (Stein, B. S., et al., *Cell*, 49:659, 1987) The RNA is then reverse transcribed to DNA and inserted into the T4+ cell's genome. Thereafter, the cell initiates replication of HIV-1 virus.

The envelope glycoprotein (gp 120) plays an important part in killing the T4+ cells, probably through cell-to-cell fusion (budding virus on the cell surface binds to other CD4+ receptors on non-infected cells). This phenomenon encompasses a syncytial reaction, resulting in the formation of giant cells consisting of both infected CD4+ cells and noninfected CD4- cells (Lifson, J. D., et al., *Science*, 232:1123, 1986). Certain populations of monocytes as well as a few other cell types express CD4+ and thus harbor the virus. The monocyte is thought to be able to bring the HIV-1 into the central nervous system. The CD4+ monocyte can thus harbor HIV-1 without dying and be a dangerous "carrier" of the virus for a long period of time.

Western Blot Assay

Western blotting is a rapid sensitive assay for detecting and characterizing proteins by utilizing the specificity an antibody has for a particular antigen. The technique can use both monoclonal and polyclonal antibodies.

The HIV-1 Western Blotting Assay used within the present invention is the conventional assay as described by Ausubel et al., *Current Protocols in Molecular Biology*, Greene Publishing Associates and Wiley-Interscience (1987). The cell proteins of HIV-infected cells are solubilized, usually with sodium dodecyl sulfate (SDS), urea, and/or other reducing agents such as 2-mercaptoethanol. Subsequently, the solubilized HIV-1-infected cell proteins are separated by sodium dodecyl sulfate polyacrylamide gel electrophoresis (SDS-PAGE) or other separatory techniques, (e.g., thin layer chromatography). The proteins are then electrophoretically transferred or blotted onto nitrocellulose paper, or other conventional suitable materials, (e.g., nylon filters), where the proteins are bound irreversibly (hereinafter an immunoblot). The paper is generally blocked to prevent non-specific binding of gp 48 antibody and is then probed with the anti-gp 48. A labelled-anti-immunoglobulin (Ig) conjugate directed towards the anti-gp 48 is added to the paper and incubated under conditions which allow the binding of the two antibodies to occur. The label on the second antibody can be conventional labels such as an enzyme (e.g., peroxidase), radioisotope or flourescent molecule.

Characterization of Anti-gp 48

Anti-gp-?is characterized by binding in the gp 48 region (46,000 to 53,000 dalton range, preferably 48,000–51,000 dalton range) upon resolution of HIV-1 infected cells having CD4 receptors in a Western Blot Assay. Western Blot strips were made from lysed HTVE cells (a continuous T lymphocytic cell line which has CD4 receptors on its cell membrane) and another H9 cell line which also has CD4 receptors on its surface to study its relation to lymphocytes. The cell lysates were treated in the same manner as if they were HIV-1 proteins, by purifying them on a sucrose gradient high-speed centrifugation (at about 110,000 G for 60 minutes), and then solubilizing the proteins in 0.1–1.0% Triton X-100 in phosphate buffered saline (PBS). It was found that gp 48, both from patients in which it was identified, and from pigs immunized with purified HIV-1, reacted with the development of a gp 48 protein band on a Western Blot assay.

The cell lines tested were continuous cell lines infected with virus or virions, which may also have oncogenes. The CD4 receptor is properly the only marker that is comparable to the T4 cell's CD4 receptor and to some monocytes CD4 receptor. The cells having CD4 receptor react with a murine monoclonal antibody called OKT4 (Ortho Pharmaceutical Corp., Raritan, N.J.). Accordingly, the reaction of anti-gp 48 with the CD4 receptor indicates that gp 48 may be part or all of the entire CD4 protein component of HIV-1, or may resemble the same.

Based upon the resolution in Western Blot assays, anti-gp 48 is characterized by its ability to bind in the gp 48 region (from 48,000 to 53,000 Daltons) of an immunoblot of solubilized HIV-1 infected cell proteins, wherein the cells have CD4 receptors. Examples of cells having CD4 receptors are selected from the group consisting of HTVE cells, CEM human T cell lymphoid cells, and MT-2 human lymphoid cells.

The Western Blot assay results upon which such characterization is based are reported in examples 3 and 4 below.

Preparation of Polyclonal Anti-gp 48

Polyclonal anti-gp 48 may be produced by immunizing an animal with purified, solubilized HIV-1 virus. Examples of animals which can be used within the present invention include humans, pigs, mice, rabbits, horses, cows, donkeys, sheep, goats, monkeys or other primates. The preferred animal is a pig. The polyclonal sera having specificity towards gp 48 is recovered by collecting blood from the immunized animal and separating the serum containing the polyclonal sera from the whole blood.

Polyclonal anti-gp 48 bind to cells having CD4 receptors, but not to cells which do not have CD4 receptors. By inhibiting binding of the gp 41, gp 160 and, to a lesser extent, the gp 120 envelope proteins, polyclonal anti-gp 48 inhibits the binding of these components of the HIV-1 virus with the CD4 receptors on T4 lymphocytes.

In accordance with this invention, the gp 48 antibodies can be produced by:

a) immunizing a pig with a purified, solubilized preparation of HIV-1 under conditions whereby anti-gp 48 antibodies are produced;

b) harvesting the antibodies by collecting blood from the pig; and c) separating the serum from the blood, the serum containing anti-gp 48 characterized on an immunoblot assay as aforesaid.

HIV-1 preparations which can be utilized in the production of anti-gp 48 are highly purified, solubilized formulations grown, for example, on serum-free, cloned lymphocyte (HTVE) systems. One such preparation is available as HIV-1 lysate, Western Blot Grade, from ProtaTek International, Inc. of St. Paul, MN. This preparation is purified by concentration of the HIV-1 virus by a series of differential concentration steps over sucrose gradients, followed by inactivation by photochemical methods or detergent/heat treatment. The preparation is characterized by greater separation between the gp 120 and 160 bands than previous HIV-1 preparations.

The anti-gp 48 can be harvested when the pig antibodies reach a titer at least equal to that of a standard HIV-1 positive control. For example, when measured by use of an Electronucleonics Enzyme Linked Immunoabsorbant Assay (ELISA) test kit with a Behring ELISA Processor II (at 492 nm), such a low positive reference value is about 0.7. Preferably, employing that reference system, the porcine anti-gp 48 is harvested at values in the range of about 0.7–2.2.

When the pig is immunized by a single vaccination with the HIV-1 preparation, and the antibodies are harvested by collecting blood from the pig within about 10 to 40 days (preferably 12 to 17 days) after vaccination, IgM anti-gp 48 is recovered. When, on the other hand, the pig is immunized by repeated vaccinations about every 14 to 120 days (preferably every 14 to 30 days), and the antibodies are harvested by collecting blood from the pig at least 20 days (preferably about 30 to 120 days) after the first such vaccination, IgG antibodies are formed.

The immune porcine IgG may be purified by precipitation with polyethylene glycol (e.g., PEG 8000) prior to use. A suitable polyethylene glycol precipitation technique has been described by Carter and Boyd (Carter, R. J. & Boyd, N. D., *J. Immunol. Methods,* 26:213, 1979). This purification method eliminates any hemolysis from the blood and removes the majority of alpha and beta globulins. IgG products having concentrations of from about 4,500 to 5,000 mg. may thus be provided, analogous to human polyethylene glycol-precipitated immunoglobulin such as "Immunoglobulin 7S Human IV," marketed by Armour Pharma of Germany. This form of immunoglobulin may be intravenously administered (see for example Stanley, P. and Cole. P., *Lancet,* I:829, 1983).

Polyclonal anti-gp 48 Activity and Use

Polyclonal anti-gp 48 has been shown to inhibit action of the HIV-1 virus on cells having CD4 receptors in vitro. Thus, in one study (Example 4 below), the effect of porcine anti-gp 48 serum on cells having CD4 receptors infected with $1 \times 10^6$ infective units of HIV-1 virus was assessed. The cells having CD4 receptors tested were HTVE, GEM, and MT-2 cells. Murine PI-M 38 cells to which $1 \times 10^6$ HIV-1 virus was added were used as control cells because murine PI-M 38 cells do not have CD4 receptors.

The various cells were incubated with different dilutions of the porcine polyclonal anti-gp 48 serum, heated to inactivate the complete system. The cells were then incubated for no more than 2 hours at 37° C. with the HIV-1 virus, prior to incubation of the cells with the immune pig sera. It was found that at certain dilutions, all the cells having CD4 receptors were lysed during incubation for 24 hours with the immune sera. On the other hand, the cells which do not have CD4 receptors incubated with the immune sera were not lysed.

Neither the treated cells which do not have CD4 receptors nor the treated cells having CD4 receptors were affected by the porcine nonimmune serum. The cells having CD4 receptors incubated as controls with nonimmune pig sera showed evidence of infection, such as giant cell formation, etc. Finally, the murine cells which do not have CD4 receptors showed no evidence of HIV-1 infection after 25 days of incubation.

Daudi (human continuous B lymphoma) cells, which do not have CD4 receptors, incubated with HIV-1 virus at the same concentration (for 2 hours at 37° C.) followed by incubation in various dilutions of porcine immune serum did not show cell lysis and were not infected by the HIV-1 virus after incubation for 1 week.

These experiments indicate that the polyclonal gp 48 antibodies tend to bind with and block the CD4 receptors in the various cells tested, thereby inhibiting access of the HIV-1 virus thereto. Such results are consistent with the further results discussed below which show that anti-gp 48 inhibits the effect of HIV-1 on other cells having CD4 receptors, e.g., the T4 lymphocytes with which the destructive effect of the virus has previously been associated.

In a second study (see Example 7 below), it has been shown that treatment of T4 cell-depleted whole blood from an AIDS patient with porcine serum incorporating anti-gp 48 substantially increased the T4 cell count without any significant change in the number of the T3, T8 or T11 lymphocyte subsets. In the noted tests, freshly drawn whole blood was treated in vitro with porcine polyclonal anti-gp 48 serum types IgM and IgG. After less than 24 hours incubation at 37° C., the T4 cell count in the treated samples almost doubled. Since all the blood-related cells and serum proteins, including T cell precursors, were present in the whole blood tested, similar results may occur in the in vivo treatment of the blood of patients having HIV-1 infections.

Like results have also been obtained in a third study in which polyclonal anti-gp-48 antibodies were added to T4 cell-depleted lymphocytes separated from HIV-1 infected blood. One batch of the lymphocytes was the "untreated" control to which nonimmune serum had been added. After incubation for only 20 hours, the number of T4 (helper/inducer) lymphocytes doubled from 7% (control) to 14%. The T8 cells (cytotoxic/suppressor subsets), which were extremely elevated in this patient, decreased from 82% (control) to 45%.

Doubling of the T4 cells in the preceding study was consistent with that noted hereinabove in connection with the in vitro treatment of whole blood from AIDS patients. Unlike the prior test, however, T8 cell depletion was noted in this study.

Passive immunization of HIV-1 infected patients can be carried out employing either the porcine purified immune IgM or IgG, depending on an evaluation of that serum which would be most effective as a treatment module. Desirably, treatment should be initiated when patients still have T4 cell populations in their blood, even if significantly depleted from normal levels.

Theoretically, the volume of immunoglobulins in humans is approximately 8% of the body mass, corresponding to 5.6 liters of blood or body fluids. An efficient dose of IgG or IgM is about 2.4 mg/10 ml of blood. A unit dose of immunoglobulins is thus about 1350 mg/dose (1344 mg/dose). The concentration of purified IgG or IgM is about 10% to 16%, w/v. A total dose is accordingly about 50 to 150 ml (preferably about 84 ml to 134 ml) over a total treatment period of 1 to 5 days. Patients so treated should thereafter be monitored with full biochemistry and lymphocyte markers. In addition, the presence of HIV-1 virus should be monitored both before the treatment and after the treatment is completed. The patient may need repeated treatment after a month if deterioration of T lymphocyte marker T4 cells and/or the continued presence of HIV-1 is recorded.

Side effects such as anaphylactic shock are possible during such treatments. Therefore, intracutaneous administration of 0.1 ml of the pig immunoglobulin is initially carried out, and the patient is monitored for an hour prior to parenteral administration of the pig immunoglobulins.

Preparation and Use of Monoclonal Anti-Gp 48

The monoclonal anti-gp-48 antibodies of the present invention can be produced by antibody producing cell lines. The anti-gp 48 antibody producing cell lines can be hybridoma cell lines commonly known as hybridomas. The hybrid cells are formed from the fusion of the anti-gp 48 antibody producing cell and an immortalizing cell line, that is, a cell line which imparts long term tissue culture stability on the hybrid cell. In the formation of the hybrid cell lines, the first fusion partner—the anti-gp 48 antibody producing cell—may be a spleen cell of an animal immunized against gp 48. The second fusion partner—the immortal cell—may be a lymphoblastoid cell or a plasmacytoma cell such as a myeloma cell, itself an antibody producing cell but also malignant. Fusions can be accomplished using standard procedures (Kohler and Milstein, (1975) (*Nature*

256,495–97; Kennett, R. (1980) in *Monoclonal Antibodies* Kennett et al., Eds. pp 365–367, Plenum Press, N.Y.).

The hybridomas are screened for production of antibody reactive with gp 48 and those which secrete reactive antibodies are cloned. The desired anti-gp-48 monoclonal antibodies can be recovered from the hybridoma supernatant using conventional techniques.

The preferred monoclonal antibodies are porcine monoclonal anti-gp 48 which can be produced by;

a) immunizing the pig with a purified, solubilized preparation of HIV-1 which, when resolved in a Western Blot assay, is characterized by binding in the gp 48 region when reacted with anti-gp 48 under conditions whereby monoclonal anti-gp 48 are produced;

b) recovering the plasma cells from the pig's spleen;

c) fusing the pig's plasma cells with myeloma cells from a pig, human or other primate, to produce hybridomas thereof;

d) eliminating the unfused, residual pig plasma cells and myeloma cells; and e) recovering the desired hybridomas.

In particular, as indicated above, the pig immunized with HIV-1 develops cells which produce antibodies of both the IgM and IgG types. When IgM antibodies are preferred, maximum titers may be obtained about 12 to 17 days after a single vaccination. When IgG is preferred, the animal is given about 3 to 5 vaccinations spaced about 14 to 30 days apart, the maximum antibody titer being obtained about 2 months after the start of immunization. The pig is given a booster dose, both subcutaneously and intraperitoneally, and 2 to 5 days thereafter it is sacrificed, and its spleen is removed and used as the plasma cell source.

The spleen is minced and the plasma cells and other lymphoid cells from the spleen are washed, preferably in RPMI 1640 medium, and fused with myeloma cells (human myeloma cells, pig malignant plasma cells or malignant plasma cells from monkeys or other primates may, alternatively, be used) using polyethylene glycol for the fusion. Preferably, human myeloma cells are used.

Following the fusion, the myeloma cells are eliminated by HAT medium (containing hypoxanthine, aminopterin and thymidine); the porcine plasma cells not previously hybridized die spontaneously within a few days. The pig/man hybridoma cells are thereafter formed and explanted in tissue culture plates for cloning and subcloning. The titer of the pig/man hybridomas which produce the antibodies raised against the HIV-1 antigen is determined by testing the supernatant from the hybridomas by reacting the antibodies in, for example, an HIV-1 ELISA system or in an appropriate Western Blot system. The desired monoclonal anti-gp 48 antibodies are thus identified, separated and recovered.

It will be understood that monoclonal antibodies against other antigens used for pig immunization may similarly be formed from appropriate pig/human hybridoma cell lines. Moreover, such monoclonals may be combined if desired. Such pig/man hybridoma cell lines and monoclonal antibodies produced thereby are more fully described in copending application Ser. No. 07/224,872, filed Jul. 26, 1988 now abandoned, directed to Hybridomas and Monoclonal Antibodies, the contents of which are hereby incorporated by reference.

The monoclonal antibodies of the present invention can be used, for example, in the production of specific positive controls, as antibodies in ELISA antigen detection systems or, preferably, in the treatment of humans. The pig/human antibodies are less immunogenic in humans than murine antibodies and are more efficient in reactions with unwanted antigens in humans (since human do not produce neutralizing antibodies against the pig/human monoclonal antibodies). Pig/human hybridomas thus have distinct advantages as compared with murine monoclonal antibodies. The present hybridomas can thus be utilized to produce AIDS virus or retrovirus monoclonal antibodies, for both in vitro diagnostic use, or for in vivo diagnostic or therapeutic application.

Those skilled in the art will appreciate that, instead of using natural antigens for pig immunization, synthetic peptides may alternatively be employed towards which pig antibodies or pig/man monoclonal antibodies can be raised in accordance with this invention.

Preparation and Use of Antiidiotype gp 48 Antibodies as a Vaccine for HIV-1 Virus Anti-idiotype gp 48 antibodies (which are specific for the variable region of the immunoglobulin) suitable for use in vaccines against the HIV-1 virus are a further feature of the present invention. The antiidiotype antibodies (Ab2) may be produced by:

a) immunizing an animal other than a pig against HIV-1 virus with a purified, stabilized preparation of HIV-1 which, when resolved in a Western Blot assay, is characterized by binding in the gp 48 region when reacted with anti-gp 48 under conditions whereby anti-gp 48 are produced;

b) harvesting the antibodies by collecting blood from the animal;

c) separating the antisera containing anti-gp 48 from the blood;

d) immunizing a pig with the antisera containing anti-gp 48 under conditions whereby anti-anti-gp 48 are produced; and e) recovering the porcine anti-anti gp 48 for use as a vaccine.

In particular, a species of animal other than a pig, e.g., a horse, cow, donkey, sheep, goat, monkey, or a different pig strain, e.g., a mini-pig, is initially immunized with HIV-1 to raise the gp 48 antibodies therein. When the appropriate immunoglobulins are thus formed, the antibodies are harvested, separated and purified, if desired, for immunization of a pig, preferably a mixed Yorkshire breed, for production of the antiidiotype antibodies.

The pig responds by producing anti-antibodies which are a template of gp 48 to whose receptors the anti-gp 48 antibody was directed.

The porcine anti-anti gp 48 is then harvested and purified on either Sepharose CNBR 4B or on another type of affinity chromatography gel to which anti-gp 48 (either as a polyclonal or as a pig/man monoclonal antibody) is coupled. The thus purified anti-anti gp 48 can then be used as a vaccine.

Alternatively, the anti-anti gp 48 idiotype antibodies may be purified, utilizing the pig as a cell factory to hybridize the immunized pig plasma cells with pig malignant plasma cells to give pig/pig hybridomas, or with human myeloma cells to give pig/human hybridomas. Such hybridomas produce antiidiotype monoclonal antibodies which can also be utilized in man as a vaccine.

In yet a further alternative, antiidiotype antibodies can be raised by first immunizing a pig with HIV-1 (gp 48) and raising the antibodies in the pig. The antibodies can then be harvested, purified and prepared for immunization in another species host such as those noted hereinabove. This technique is preferred when producing antiidiotype antibodies as vaccines for animals.

From the preceding, it will be seen that HIV-1 virus or the corresponding synthetic peptide can be simulated as an antiidiotype antibody, with the thus-produced anti-anti AIDS proteins or constructed antigens being created from the templates of specific antibodies from another animal.

Immunoassays Using Anti-gp 48

The anti-gp 48 antibodies are useful in a variety of procedures for detecting the presence or absence of HIV-1 in a sample or the amount of gp 48 in a sample. For this purpose the anti-gp 48 antibodies can be used in a number of different immunoassays for HIV-1. These include radioimmunoassays, enzyme linked immunoabsorbent assays (ELISA), immunofluorescent detection methods, sandwich assays, agglutination assays and precipitation assays of the conventional types.

For many of these assays an immunoabsorbent is formed by attaching an anti-gp 48 antibody to a solid phase. In a competitive immunoassay (e.g., radioimmunoassay) for gp 48, a sample of the biologic fluid to be assayed is contacted with the immunoabsorbent. The mixture is incubated after which a predetermined amount of labelled HIV-1 antigen is added. After further incubation, the immunoabsorbent with the bound HIV-1 antigen is separated from the free antigen and the activity of the label in the bound or free group antigen fraction is measured in order to determine the amount of gp 48 in the sample. In such assays, the label may be a radioisotope (radioimmunoassay), an enzyme, or a fluorescent compound.

In an ELISA, the biological fluid is contacted with the solid phase such that the antigens from said fluid are absorbed onto the solid phase. The anti-gp 48 antibody is placed in contact with the immunoabsorbent under conditions (e.g., incubation) whereby the antibody is allowed to bind to the appropriate antigen. Subsequently, a second labelled antibody directed towards the anti-gp 48 antibody is added and incubated under conditions which allow binding to occur. The substrate for the enzyme is added and the absorbance of the solution is measured using a spectrophotometer. Alternatively, in an ELISA the anti-gp 48 antibody may be directly labelled with an enzyme.

Fluorescent microscopy can also be used to observe the presence or absence or quantity of anti-gp 48 antibodies in a sample. In one form, the anti-gp 48 antibodies themselves are labelled with the fluorescent compound such as fluorescein, and then brought into contact with a biological sample. In an alternate format, unlabelled anti-gp 48 antibodies are contacted with the biological sample and then a second fluorescently labelled antibody directed against the anti-gp 48 antibody is added. In either format, binding of the anti-gp 48 antibodies to the biological fluid can be monitored under a microscope.

The preferred immunoassay of the present invention is the sandwich immunoassay. The sandwich immunoassay can be used in a variety of formats using either monoclonal antibodies on both sides, a monoclonal on one side and a polyclonal on the other side, or polyclonals on both sides. Further, the sandwich assay can be forward, reverse, or simultaneous sandwich assay as described in U.S. Pat. No. 4,376,110 issued Mar. 8, 1983, the contents of which are hereby incorporated by reference.

In one format, an immunoabsorbent is formed by attaching an anti-gp 48 antibody to a solid phase. Biological fluid is contacted with the immunoabsorbent under conditions (e.g., incubation) which allow binding of the antibodies to the gp 48 protein to occur. Subsequently, a second labelled monoclonal antibody reactive with gp 48 is added to the mixture under conditions (e.g., incubation) which allow binding to occur between the second antibody and gp 48 antigen. The label of the bound antibody is measured as an indication of the presence or absence or the quantity of gp 48 in the sample.

Another format for a sandwich assay uses both a monoclonal antibody and polyclonal antibodies. The monoclonal antibody can be used as either capture antibody or the detector antibody. When used as the capture antibody, an immunoabsorbent is formed by attaching the monoclonal antibody to a solid phase. The biological fluid to be tested is contacted with the immunoabsorbent under conditions (e.g., incubation) which allow binding of the antibody to the antigen to occur. Subsequently, labelled polyclonal antibodies are added to the biological fluid under conditions (i.e., incubation) which allow binding to occur. The label of the bound or the free antibody can be measured as an indication of the presence or absence of gp 48 in the sample. The above sandwich assays can be modified such that they become indirect sandwich assay wherein the detector polyclonal antibodies or monoclonal antibody is not labelled and a labelled antibody directed toward the detector polyclonal antibodies or monoclonal antibody are added to the reaction mixture under conditions (e.g., incubation) which allow binding of the labelled antibody to the anti-gp 48 antibody to occur.

The above-described immunoassays can be used to quantitate the gp 48 in a sample by establishing a standard curve. A standard curve relating quantity of gp 48 to a value indicative of the amount of the particular of the label, (e.g., Absorbance) can be established using standards having known gp 48 content. After preparation of such a curve, the quantity of gp 48 in a sample can be determined by extrapolating a quantity of gp 48 from the curve upon obtaining a value indicative of the amount of label (e.g., absorbance). The assays described above would provide physicians with a quick and reliable method of determining whether an individual is afflicted with HIV-1.

Diagnostic kits for performance of the assays described above can include monoclonal anti-gp 48 or labelled anti-gp 48 or mixtures of labelled or unlabelled antibody is in a container. The kits may further include a solid phase having a monoclonal gp 48 antibody or polyclonal gp 48 antibodies absorbed thereon.

Gp 48 can be isolated from the biological samples using conventional protein separation techniques, e.g., gel electrophoresis and affinity chromatography. (Ausebel et al *Current Protocols in Molecular Biology*, (1987)). The term gp 48 is intended to encompass the entire protein and portions thereof. A portion of gp 48 is defined as that portion of the antigen which will bind with polyclonal and monoclonal antibodies specific for gp 48.

Upon isolation, gp 48 can be sequenced using conventional genetic engineering techniques. A synthetic polypeptide can be produced having the same or similar amino acid sequence as gp 48. A similar amino acid sequence is defined as an amino acid sequence having substantial homology or being capable of performing the same biological function. The isolated gp 48 or a portion thereof or the synthetic polypeptide sequence having the same amino acid sequence as gp 48 or a portion thereof can be used in vaccines against HIV-1.

The invention will now be further illustrated by the following examples.

EXAMPLE 1

Identification of gp 48 Antibodies in Human Patients

A first patient (Patient No. 1) was a female kidney dialysis patient who had received numerous blood transfusions and had had one unsuccessful kidney transplant. The patient had no AIDS or ARC symptoms. The patient seroconverted with the appearance of a gp 48 bank on a Western Blot assay employing a high-purity, solubilized HIV-1 lysate (HIV-1 lysate, Western Blot Grade, ProtaTek, Inc.). The presence of the gp 48 antibodies was not independently confirmed by Western Blots on other more impure lysates.

A second patient (Patient #2) was a 23-year-old female IV-drug user who was tested prior to an induced abortion. The patient had no signs of AIDS or Aids-Related Complex (ARC). She died 14 days after induction of the abortion from disseminated intravascular coagulation during profuse uterine bleeding. The serum sample from the patient was HIV-1 Ab ELISA positive; upon Western Blot assay, gp 48 antibodies were resolved. After further Western Blot assays employing different HIV-1 lysates, the presence of the anti-gp 48 was independently confirmed.

A third patient (Patient #3), a female, had received numerous cryoprecipitates and Factor VIII products because of a yon Willebrands bleeding disorder for several years. The patient had not developed any AIDS or ARC symptoms. She was found to be HIV-1 ELISA positive, and anti-gp 48 was detected on Western Blot assay. Strip 1 in FIG. 1 is a drawing illustrating the proteins identified on the nitrocellulose strip obtained in a Western Blot assay of serum from this patient. The strip shows protein banding at gp 48 and 160, as well as narrow bands, inter alia, at p 53 and p 55.

A fourth patient (Patient #4), a male suffering from metastatic carcinoma, had received multiple blood transfusions for a number of years. He had not developed any AIDS or ARC symptoms. His blood was found to be HIV-1 ELISA positive, and the presence of gp 48 was identified by Western Blot.

A fifth patient (Patient #5) was a 30-year-old female who had no overt symptoms when tested for HIV-1 antibodies. She was pregnant (first month, first trimester) and had previously used IV drugs under unhygienic conditions. Conception had occurred with a homosexual male, prompting the test. The patient's blood was found to be anti-gp 48 positive.

A sixth patient (Patient #6), the last-mentioned homosexual male, was also tested; his blood was classical HIV-1 antibody positive, displaying banding at p 24, gp 41, p 53, p 55, p 64, pg 120 and gp 160.

Preparation and Characterization of Anti-gp-48

EXAMPLE 2

Preparation of Anti-gp 48 by Immunization

A pig of mixed Yorkshire breed (appr. 60 pounds in weight) was vaccinated once with the above-identified purified HIV-1 lysate.

The HIV-1 was solubilized in Triton X100 in PBS buffer, pH 7.4. The concentration of the solubilized HIV-1 was approximately 100 ug/ml. 1 ml of the HIV-1 was mixed with 1 ml of Freund's complete adjuvant immediately prior to immunization of the pig. The vaccination was performed subcutaneously on 4 different locations on the pig's neck.

Blood was drawn from the pig's ear vein 15 days after the vaccination to test for the presence of IgM-specific HIV-1 antibodies. Serum was separated by centrifugation and tested for the presence of IgM using an ElectroNucleonics HIV-1 ELISA Test Kit. The antibody titer was measured. Goat antihuman IgM horseradish peroxidase (Calbiochem, Cat. #401904) at a dilution of 1:2000 was used to detect IgM binding. The serum was also tested on HIV-1 Ab Western Blot nitrocellulose strips using the method.

Porcine serum drawn from the pig prior to the vaccination was tested for a baseline value. The pig serum tested positive for IgM anti HIV-1 ELISA (0.626) with the cut-off (that value regarded as positive for HIV-1) at 0.189. The IgG anti HIV-1 was found to be 0.031 (far below the cut-off). In the HIV-1 Ab Western Blot assay, the IgM anti HIV-1 serum showed gp 48 as a diffuse broad band ranging from a molecular weight estimated to be at 48,000 Daltons to about 53,000 Daltons. A gp 160 band (160,000 Daltons) was also observed. Weak gp 120 (120,000 Daltons) and p 24 (HIV-1 core) bands were also observed. No gp 41 (HIV-1 envelope) band was detected. Strip 2 in FIG. 1 shows the principal banding resolved in the Western Blot of this serum.

The pig was revaccinated with the same batch of solubilized HIV-1 without Freund adjuvant. (100 ug HIV-1 /ml 0.1%–1% Triton X100 in PBS, pH 7.4) every 14 days (5 times). Blood was drawn from the ear vein just prior to each vaccination and tested for the presence of IgM and IgG HIV-1 antibodies in HIV-1 ELISA and on the aforesaid HIV-1 Ab Western Blot assay.

Figure 2:
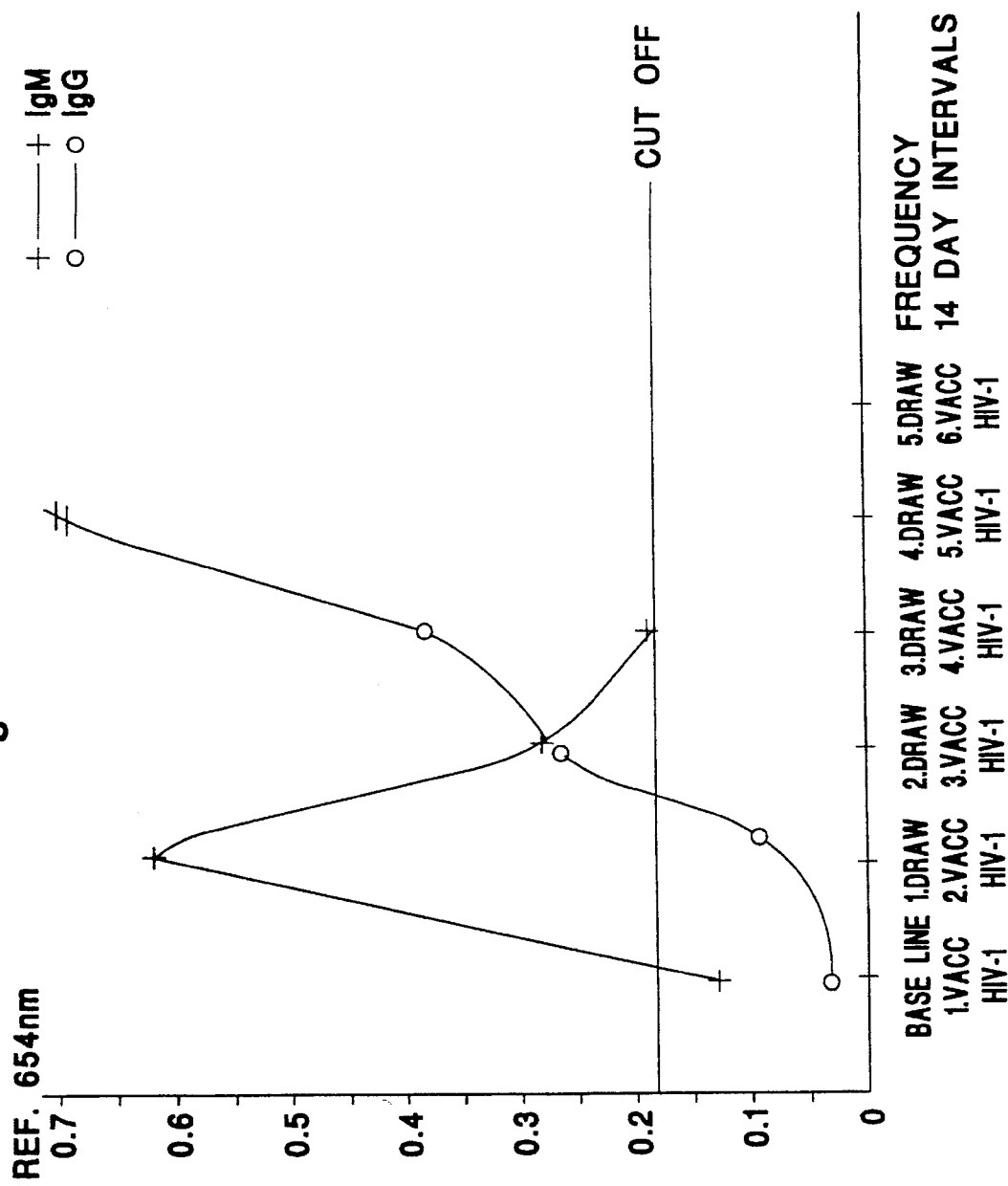
FIG. 2 is a plot of the IgM and IgG titers obtained in an (Enzyme Linked Immunoassay) ELISA assay of the porcine sera obtained upon successive revaccinations of a pig in the immunization described in Example 2.

FIG. 2 shows the IgM and IgG titers determined in the ELISA assay, concurrently with each vaccination. The IgG titers exceeded the IgM titers commencing 28 days after the initial vaccination. Upon resolution by the same Western Blot assay described above, each serum sample exhibited a gp 48 band but no gp 41 band.

Characterization of Anti-gp 48

EXAMPLE 3

Selective Inactivation of T4 Cells Having CD4 Receptors by Porcine Anti-gp 48

The porcine IgM anti-gp 48 serum and porcine IgG anti-gp 48, prepared as described in Example 2, were sterilized using psoralen/ultraviolet irradiation, and retained in sterile containers. Porcine serum from nonimmunized pig was used as a porcine serum control. None of the porcine sera were heat-activated.

60 ml of whole blood was withdrawn from a healthy HIV-1 Ab negative female volunteer into tubes containing anticoagulantia (ACD). The lymphocytes were separated by an independent laboratory, using Hypaque Ficoll gradient centrifugation. The cells were washed once in RPMI 1640 (Gipco) and reconstituted in RPMI 1640 to a volume of about 5 ml. The total amount of lymphocytes was estimated to be about $7.5 \times 10^7$.

4.9 ml of RPMI 1640 was added to each of 12 sterile petri dishes (diameter 5 cm). To each petri dish was added 100 ul of the lymphocyte concentrate constituting about $6 \times 10^6$ cells per petri dish, or about $1.3 \times 10^6$ cells/ml. To the first group of three petri dishes was added fetal bovine serum (FBS) at concentrations of 1:32, 1:64 and 1:128, respectively. To the second group of three petri dishes was added psoralen/UV treated nonimmunized porcine serum at dilutions of 1:32, 1:64 and 1:128. To the third group of three petri dishes was added HIV-1 immunized IgM anti-gp 48 serum at dilutions of 1:32, 1:64 and 1:128, respectively. To the fourth group of three petri dishes was added HIV-1 immunized IgG anti-gp 48 porcine serum at dilutions of 1:32, 1:64 and 1:128, respectively.

All the petri dishes were then incubated in a 37° C., 5% $CO_2$ incubator for 20 hours. After standing overnight, the contents of the several petri dishes were transferred to sterile, closed plastic tubes and held at room temperature overnight. The next morning the contents of the several plastic tubes in each group were batched, because the number of lymphocytes stemming from each petri dish was not sufficient for cytophotometric measurement.

The lymphocytes from the four different groups were tested for the presence of T4 and T8 cells on an Ortho Flow cytophotometer; the individual who carried out the cytophotometry was given only blindly coded groups of lymphocytes to measure. An internal control consisting of Hypaque Ficoll-separated lymphocytes from a healthy volunteer was also measured.

The percentage of T4 cells in the internal control group (identified as Group I) was 50%, while the percentage of T8 cells was 28%. The T4/T8 ratio was 1.79.

In Group II (lymphocytes incubated with FBS), the T4 cell population was 52% and the T8 population was 23%. The T4/T8 ratio was 2.26 (normal values).

In Group III (lymphocytes incubated in non-immunized porcine serum) the proportion of T4 cells was 54% and T8 cells 16%. The T4/T8 ratio was 3.37.

In Group IV (lymphocytes incubated with porcine IgM anti-gp 48) the T4 percentage was 25% (abnormally low value) and T8 was 22% (normal value). The T4/T8 ratio was lower than the controls (1.14).

In Group V (lymphocytes incubated with porcine IgG anti-gp 48) the T4 was 7% (extremely low value) and the T8 was 26% (normal value). The T4/T8 ratio was found to be extremely low (0.27).

Figure 3:
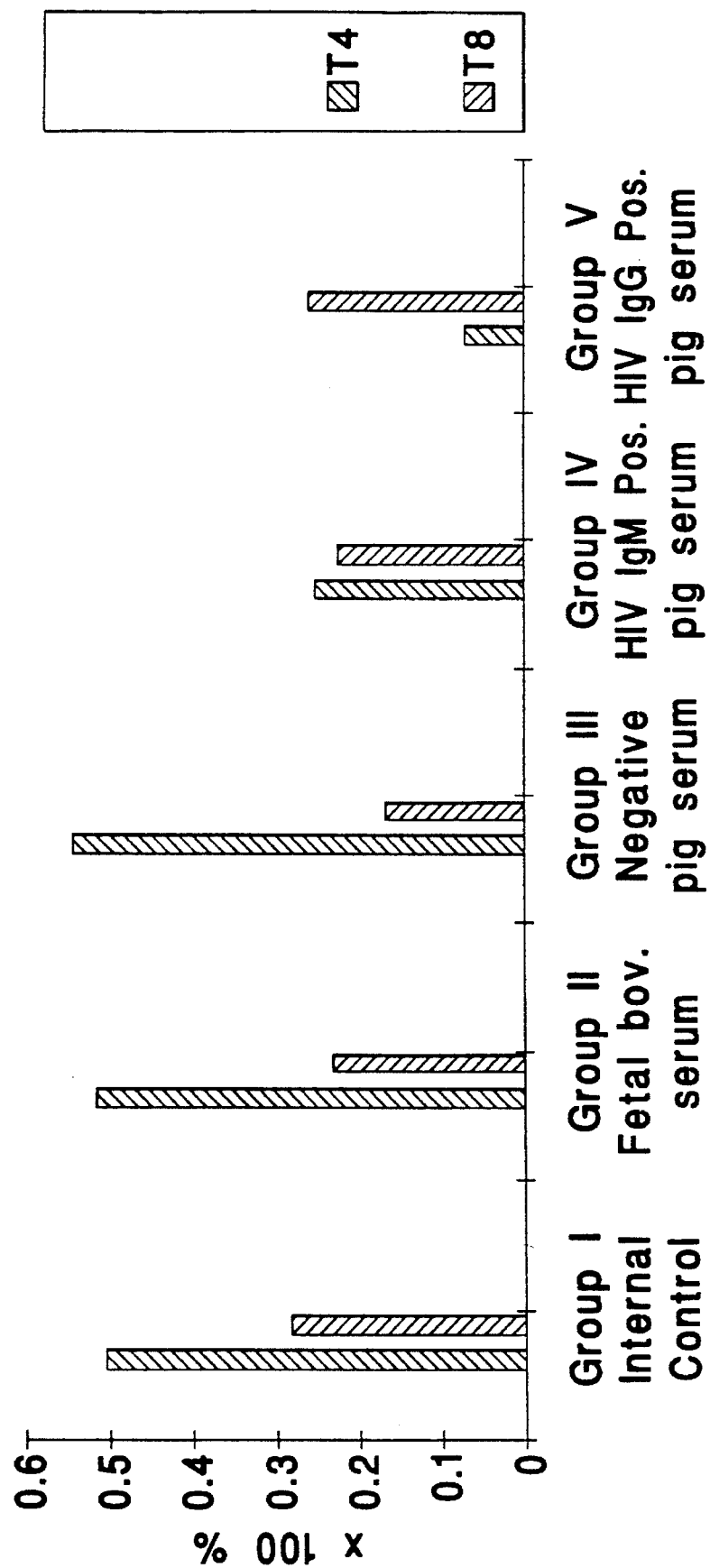
FIG. 3 is a graph illustrating the relative T4/T8 cell populations in lymphocyte mixtures treated in the experiment of Example 3.

The percentages of the T4 and T8 cells present in the respective test groups are plotted in FIG. 3 of the drawings. The data indicate that the T4 cell population is significantly lowered (probably due to the combination of induced lysis and the fact that an abnormally high number of null (non-reacting) cells were detected by neutralization or binding of the porcine anti-gp 48 to the T4 or CD4 receptor. The porcine IgM anti-gp 48 serum, and particularly the porcine IgG anti-gp 48 serum, thus prevented binding of the fluorescent OKT4 monoclonal antibody to the T4 cells.

On the other hand, neither of the anti-gp 48 sera had any effect on the T8 cells, and the serum from the nonimmunized pig did not affect the T4 or T8 cell populations.

Thus, the anti-gp 48 sera appear to selectively inactivate CD4 receptors on the T4 lymphocytes, and might even lyse the cells under certain conditions. It is of course possible that binding of the IgG or IgM may have initiated a complement-induced lysis (the porcine serum was not heat-inactivated).

EXAMPLE 4

Characterization of Anti-gp 48 by Effects on Receptors in Different Cell Lines

Continuous cell lines known to contain varying proportions of CD4 receptors were incubated with various test and control sera, to study the effect of the sera on the binding of OKT4 monoclonal antibodies to the cells.

The following cell lines were employed:

HTVE—T lymphoma cell line, immortalized by oncogenes

CEM—T lymphoma cell line, immortalized by oncogenes

MT-2—T lymphoma cell line, infected with HTLV-1

PI-M35—mouse macrophage continuous cell line, probably immortalized by virus of unknown type Daudi—B cell line from a patient with Burkitt's lymphoma Binding of the fluroscein isothionate conjugated antibody to the respective cells was measured on an Ortho cytophotometer. Northern blot analyses of total RNA from Daudi cells were also performed using nick-translated oncogene probes (Motoo, Y. et al., *Biochem. Biophys. Res. Comm.* 135:262 (1986)). The Daudi cells expressed the following oncogenes, c-ab1, c-fes, c-fms, c-myc, c-IIa-ras, and c-sis. HIV-1 infectivity of the cell lines tested was also compared.

The following results were observed:

TABLE I

| Characteristics of Cell Lines Tested | | |
|---|---|---|
| Cell Line | HIV-1 Infectivity | OKT4 Binding |
| HTVE | +++ | 7% |
| CEM | +++ | 79% |
| MT-2 | +++ | 14% |
| PI-M38 | 0 | <1% |
| Daudi | 0 | <1% |

From the table it can be seen that the CEM cells have the highest percentage of CD4 receptors. The percentages found were lower than expected for the HTVE and MT-2 cells. The sizes of the cells measured were 15 to 18 microns, whereas lymphocytes are generally about 12 microns. Higher percentages of CD4 receptors may not have been noted since the cytophotometer (which had a 12-micron gate) may not have recognized all OKT4 bound cells. Alternatively, the relatively low CD4 percentages noted may indicate that the CD4 receptors were not sufficiently exposed on the cell membranes.

On the other hand, the cells treated were readily infected by HIV-1 (about 90% of the HTVE, CEM and MT-2 cells were infected).

The cell lines were treated with porcine anti-gp 48 immune sera prepared as described in Example 2 above, and control sera, together with HIV-1 (2.5 KS 050988) at an activity of 10 infective units per ml, as follows:

1. Various test cells were incubated with HIV-1 at 37° C. for 2 hours in 24 well plates, and then immune porcine sera and control sera were added thereto;

2. Immune porcine sera and control sera were added to the cells in 24 well plates, incubated for 2 hours, and then the HIV-1 was added thereto; and 3. Immune porcine sera and control sera plus the HIV-1 were added directly to the cells in 24 well plates, in a dilution of 1:50.

All sera used for incubation were diluted in RPMI 1640 and 10% fetal bovine serum FBS as follows: 1:1, 1:8, 1:32, 1:128, 1:512. The plates were read after every 24 hour period under phase microscopy. General cell morphology of the cells was noted, especially viability, giant cell, syncytia formation, cytopathic effect (CPE) and lysis.

Surprisingly, approximately 90% of the HTVE, CEM and MT-2 (susceptible to HIV-1 transfection) cells were lysed at a serum dilution of up to 1:128 of the heat treated (56° C., 30 minutes) immune porcine sera and control sera (but not by the anti-gp 48 negative control serum). The PI-M38 mouse macrophages and Daudi cells were not lysed and were not susceptible to the HIV-1 virus.

It should be noted that the amount of virus added ($10^6$ infective units/ml) to the various cells was probably 100 to 1000 times higher than what would be detected in HIV-1 infected patients when they have viremia outbursts. The experiment suggests, however, that there may be both an antilymphocytic factor and antiviral factor(s) present in the porcine anti-gp 48 serum types IgM and IgG.

In further in vitro studies, the antilymphocytic activities of the test cell lines have been shown to be related to T4 cells. Thus, the porcine anti HIV-1 IgM and porcine anti HIV-1 IgG reacted with the continuous cell lines, as indicated in Table 2:

TABLE 2

Lysis of Different Cell Lines by Pig Anti-gp 48

| Cell Line | HIV-1 Infectivity | % Lysis by Pig IgM Anti-gp 48 | By Pig IgG Anti-gp 48 |
| --- | --- | --- | --- |
| HTVE | +++ | 90% | 90% |
| CEM | +++ | 90% | 90% |
| MT-2 | +++ | 90% | 90% |
| PI-M38 | 0 | <1% | <1% |
| Daudi | 0 | <1% | <1% |

From Table 2, it may be seen that the cell lines infected with HIV-1 also had the highest cell deaths. Slightly more cells were lysed from incubation with the porcine immune IgM serum as compared with the percentage of cells lysed with the porcine immune IgG. In both cases, however, the porcine anti-gp 48 preferentially bound to and lysed the cell lines having CD4 receptors as compared with the cell lines which do not have CD4 receptors.

EXAMPLE 5

Blocking Binding Sites of Other HIV-1 Antibodies with Anti-gp 48

The effect of anti-gp 48 on the resolution of other protein constituents of HIV-1 was determined by Western Blot assays employing strips pretreated by absorbing anti-gp 48 sera thereon. In initial experiments (part (a) below), anti-gp 48 serum from patient No. 4 (see Example 1 above) was preabsorbed on the Western Blot strips; in further experiments (part (b) below), the pig anti-gp 48 serum (type IgM and IgG) prepared as described in Example 2 was precoated on the strips.

a) Absorption of Anti-gp 48 from Patient No. 4

Serum from the patient with yon Willebrands disease (Patient No. 4) was diluted 1:100 in PEG 8000 (5% w/v) in PBS-Tween 20 in 5% w/v nonfat milk proteins. Three ml of the diluted serum was added to HIV-1 Quick Western Blot strips prepared as described in the aforesaid Example 2 of U.S. application Ser. No. 099,311 and incubated for 2 hours in a slotted tray at room temperature with gentle agitation. As a control, human HIV-1 antibody negative serum was diluted in the above-described buffer. Three ml of the diluted serum as added to HIV-1 Quick Western Blot nitrocellulose strips in a slotted tray and incubated for 2 hours at room temperature with gentle agitation.

Following incubation, the Quick Western Blot strips were washed 4 times (1 minute each time) with PBS-Tween buffer to remove excess unbound protein. The strips were then incubated with sheep antihuman IgG (Calbiochem #554826) at a dilution of 1:500 in PBS-Tween buffer. 3 ml of the diluted antibodies were added to each strip in a slotted tray and incubated at room temperature for 2 hours with gentle agitation. The strips were then washed 4 times (1 minute each time) to remove excess unbound sheep proteins.

The strips were then incubated with:

(i) HIV-1 Western Blot Positive serum (ProtaTek HIV-1 Western Blot Lysate Grade) which resolved the following HIV-1 Ab bands: p28, p24, p31/33, gp 41, p53 (p51), p55, p64 (p66), gp 120 and gp 160 (see strip 1 in FIG. 1). The test serum was diluted 1:20 in PEG-PBS-Tween-5% w/v nonfat milk protein buffer;

(ii) Serum from Patient No. 1, diluted 1:20 in the last-mentioned buffer;

(iii) Porcine serum immunized with HIV-1 (gp 48 positive) diluted, as described in Example 2 above, 1:20 in the same buffer; or (iv) Serum from Patient No. 6, diluted 1:20 in the above buffer.

All the Quick Western Blot strips (both those pretreated with the serum from Patient No. 4, and those strips coated with the HIV-1 negative serum) were incubated in the tray at room temperature for 15 minutes with gentle agitation. The strips were washed with PBS-Tween 4 times (1 minute each time) to remove excess unbound proteins. Goat anti-human IgG horseradish peroxidase conjugate (ProtaTek, Lot M) was diluted 1:500 in PBS-Tween. 3 ml of the diluted conjugate was added to the strips and incubated for 15 minutes at room temperature with gentle agitation. The strips were washed 4 times (1 minute each time) in PBS-Tween and once (1 minute) in PBS alone.

3,3'-diaminobenzidine tetrahydrochloride dihydrate (DAB) (Aldrich Chemical Co., Milwaukee, Wis.) was diluted in PBS containing hydrogen peroxide (50 mg DAB/ 100 ml) for use as a substrate (chromogen). 3 ml was added to each strip and color reactions were obtained when incubated with the strips for 10 minutes with gentle agitation. The strips were then studied for protein bands.

It was found that gp 41 and gp 120 were not bound to the strip pretreated with the porcine anti-gp 48 and tested with the HIV-1 Ab positive serum [(iii) above], gp 160 being the only visible envelope protein. No other bands were altered. However, the strip revealed a weak gp 48 binding (as contrasted with the strip tested with the anti-gp 48 serum from Patient No. 1 [(ii) above]. Another protein, gp 90, which is rarely seen as a diffuse band on HIV-1 Ab positive strips (this protein is known to be a highly glycosylated protein reported to be related to the HIV-1 envelope), became more dense and visible on anti-gp 48 pretreated strips.

Strips pretreated with the negative serum had all the HIV-1 specific bands which exhibited binding on the strips tested with HIV-1 antibody-containing serum.

Thus, Quick Western Blot strips pretreated with HIV-1 Ab negative serum do not prevent HIV-1 Ab specific proteins from appearing.

The strips pretreated with anti-gp 48 serum and tested with anti-gp 48 sera from other patients and from the HIV-1 Ab positive pig (showing the presence of the gp-48 band) showed binding of gp 48. Therefore, HIV-1 Ab positive serum containing all HIV-1 specific bands, including gp 120 and gp 41 on strips which have been pretreated with anti-gp 48 serum, do not bind gp 160 and gp 41.

The neutralization effect by anti-gp 48-pretreated Quick Western Blot strips apparently blocks binding sites for antibodies (HIV-1 Ab) of the type of envelope proteins gp 160 and gp 41 and, to a certain extent, gp 120, which may be part of or the entire binding site for anti-gp 120 and anti-gp 41.

b) Absorption of Porcine Anti-gp 48

Porcine serum containing anti-gp 48 [see (a)(i) above] was diluted in PEG 8000, 5% w/v in PBS-Tween with 5% w/v nonfat milk proteins to a dilution of 1:50. HIV-1 Quick Western Blot strips were incubated with the diluted porcine serum (3 ml per strip) in a slotted tray for 2 hours at room temperature with gentle agitation, and then washed. The strips were reincubated with sheep antihuman IgG (Calbiochem #554826) at a dilution of 1:500 following the same procedure described in part (a) above.

The pretreated strips were subjected to assay by Quick Western Blot. A first strip tested an HIV-1 Ab positive serum sample. A second strip was incubated with anti-gp 48 serum from Patient No. 1, a third strip with porcine HIV-1 positive serum, and a fourth strip with anti-gp 48 serum from Patient No. 6. Nonpretreated HIV-1 Quick Western Blot strips were tested with the same serum samples.

As in the case of the pretreatment of the strips with anti-gp 48 human serum (part (a) above), the porcine anti-gp 48 serum pretreated strips did not bind gp 160 and gp 41 from the HIV-1 Ab positive patient (whose serum blotted all the known HIV-1 proteins, including gp 160, 120 and gp 41, on the untreated strip). Thus, the porcine anti-gp 48 serum, like the anti-gp 48 human serum, neutralizes or prevents binding of antibodies to gp 160, gp 41 and; to a certain extent, gp 120.

Based on the preceding experiments, it has been found that solubilized HIV-1 lysate produces antibody to gp 48 in pigs, which prevents antibody binding of antibodies to gp 160, gp 41 and, to a certain extent, gp 120.

Effect of Anti-gp 48 on T4 and Other

EXAMPLE 6

Effect of Anti-gp 48 on Other Lymphocytes from the Whole Blood of a Health Subject 60 ml of whole blood was drawn from a 36 year old health female (HIV-1 Ab negative and HIV-1 Quick Western Blot negative). The blood was drawn in tubes containing ACD anticoagulantia. 5 ml of whole blood was drawn in a tube for white cell count. To the freshly drawn blood were added: a) porcine anti-gp 48 IgM type serum, b) porcine anti-gp 48 type IgG serum, c) partially purified anti-gp 48 type IgG, and d) an untreated control.

The partially purified IgG-type anti-gp 48 was purified using a method described by Carter, R. J. and N. D. Boyd, J. Immunol. Methods 26:213 (1976). The psoralen/UV treated sera and partially purified anti-gp 48 IgG were added to the whole blood at a dilution of 1:50. The IgG concentration prior to dilution in the partially purified product was measured as 1,021 mg/100 ml; in the anti-gp 48 serum, the IgG concentration was measured as 1,103 mg/100 ml using Behring Diagnostics NOR-partigen plates.

Each blood sample was incuated for 2 hours at room temperature on a tube rocker followed by incubation at 37° C. for 20 hours. The lymphocytes were isolated from the whole blood by an independent laboratory using Hypaque-Ficoll gradient centrifugation. The lymphocytes were then reacted with OKT4 monoclonal antibody and OKT8 monoclonal antibody, and blind-coded for cytophometric measurement. The lymphocyte populations were measured on an Ortho Flow cytophotometer having an approximately 12 micron gate. The following cell populations were determined:

TABLE 3

Effect of Treatment of T4 and T8 Cell Populations of Health Subject with Anti-gp 48

| Lymphocyte Marker | Percentage of Cells | Absolute Numbers/sq mm |
|---|---|---|
| A. Whole Blood-Treated with Anti-gp 48, IgM | | |
| OKT4 | 58 | 2544 |
| OKT8 | 35 | 1535 |
| B. Whole Blood Treated with ANti-gp 48, IgG | | |
| OKT4 | 55 | 2413 |
| OKT8 | 18 | 1228 |
| C. Whole Blood Treated with Anti-gp 48, Semipure IgG | | |
| 56% | 56 | 2457 |
| 31% | 31 | 1360 |
| D. Untreated Whole Blood | | |
| OKT4 | 53 | 2325 |
| OKT8 | 33 | 1448 |

Table 3 shows there were no significant changes in the percentages of OKT4 and OKT8 cells in the anti-gp 48-treated whole blood, as compared with the untreated whole blood. Accordingly, it appears that anti-gp 48 does not alter the proportion of T4 and T8 cells in a healthy subject.

EXAMPLE 7

Anti-gp 48 Treatment of AIDS Whole Blood

A 35-year hold homosexual male without AIDS or ARC who was previously found to be HIV-1 ELISA positive and confirmed HIV-1 Ab Quick Western Blot positive (p 18, p 24, p 31/33, gp 41, p 53, p 55, p 64, gp 120, gp 160), and was rechecked and found to have the same HIV-1 antibodies about a year later was used for this experiment. 60 ml of blood was drawn for the lymphocyte experiment and 5 ml was drawn in one tube for a white cell count.

To the patient's freshly drawn whole blood was added: a) pig anti-gp 48 type serum, b) pig anti-gp 48 type IgG serum, c) a nonimmune pig serum, and d) a nontreated control. The sera were inactivated by psoralen/UV treatment and added in a dilution of 1:50.

The tubes were placed on a rocker for 2 hours at room temperature, and then placed on a rocker at 37° C. for 20 hours. The tubes containing the whole blood were then transferred to an independent laboratory where the lymphocytes were isolated using Hypaque-Ficoll gradient centrifugation. The lymphocytes were then reacted with OKT3, OKT8 and OKT11 monoclonal antisera.

The white cell count was obtained and the lymphocyte populations were determined in a blind study on an Ortho Flow cytophotometer. The following results were obtained:

A. In the porcine anti-gp 48 IgM treated, the T4 cells increased from 196 per mm (16%) to 331 per mm (27%).

B. In the porcine anti-gp 48 IgG treated, the T4 cells increased from 196 per mm (16%) to 368 mm (30%).

The other T-cell subsets did not change significantly, except for a minor decrease in the T11 from 078 per mm to 956 per mm in the anti-gp 48 IgG treated set.

The cell populations, determined by binding of the monoclonal antibody markers, are set forth in Table 4 below.

TABLE 4

Effect of Treatment of HIV-1 Infected Lymphocytes with Anti-gp 48

| Lymphocyte Marker | Percentage of Cells | Absolute Numbers/ mm$^2$ |
|---|---|---|
| A. 46% of Cells within Gated Lymphoid Region of Control | | |
| % Background | 1 | — |
| OKT3 | 73 | 894 |
| OKT4 | 27 | 331 |
| OKT8 | 58 | 711 |
| OKT11 | 86 | 1054 |
| T4/T8 | — | 0.5 |
| B. 32% of Cells within Gated Lymphoid Region of Control | | |
| % Background | 1 | — |
| OKT3 | 73 | 894 |
| OKT4 | 30 | 368 |
| OKT8 | 58 | 711 |
| OKT11 | 78 | 956 |
| T4/T8 | — | 0.5 |
| C. 50% of Cells within Gated Lymphoid Region of Control | | |
| OKT3 | 77 | 943 |
| OKT4 | 16 | 196 |
| OKT8 | 59 | 723 |
| OKT11 | 88 | 1078 |
| T4/T8 | — | 0.3 |

As may be seen from Table 4, upon treatment with either of the IgM or IgG specific antibodies, the number of T4 cells doubled after about 22 hours incubation. Since T4 cell depletion is regarded as a typical sign of approaching immune paralysis, effecting an increase in the serum T4 cell population of an AIDS patient would be of significant advantage in HIV-1 therapy.

Preparation of Monoclonal and Anti-idiotype Antibodies of Anti-gp 48

EXAMPLE 8

Preparation of Monoclonal Anti-gp 48

Monoclonal antibodies are prepared in accordance with the invention by immunizing a pig as more fully described in Example 2 above, and when a sufficient titer is obtained (IgM or IgG-specific, as may be desired), the animal is given a booster vaccination (e.g., about 50 ug HIV-1 subcutaneously (sc), and about 50 ug HIV-1 intraperitoneally (i.p.), sacrificed, and the antibodies are recovered from the spleen cells.

The spleen is handled under aseptic conditions, being cut into appropriate pieces and the pieces thereafter being gently teased apart using a pair of forceps. The cells are washed twice in IMDM (Grand Island Biological, Grand Island, N.Y.) or RPMI 1640, and the cells thus obtained are then resuspended to a concentration of 5 to 10×10$^6$/ml.

Human myeloma cells from IgG2 kappa secreting myeloma cell line G 4672 B (normally used for human/human hybridoma cell lines) is 6-cycloguanidine-sensitive and is therefore well-suited for porcine/human hybridoma cell-line production. The cells are grown at logarithmic growth phase, washed twice in RPMI 1640 with 10–20% FBS. The cells are collected in logarithmic growth phase and washed twice in RPMI 1540 (or IMDM).

The cells are then pelleted with 10$^8$ spleen cells in the ratio of 3:1 (myeloma cells:immunocytes) in a 16×125 mm tissue culture tube (Corning Labware, Corning, N.Y.). Fusion is performed under sterile conditions in a 37° C. water bath using a modification of Oi and Hersenberg (Foster, C., Cancer Treat. Rev. 9:59 (1982); Oi, V. T. and L. A. Herzenberg in: B. B. Mishell and S. M. Shiigi (Eds), Selected Methods in Cellular Immunology, pp 351–372, W. H. Freeman Co., San Francisco, Calif. (1980). One ml of polyethylene glycol (average molecular weight, 1500; Aldrich Chemicals, Milwaukee, Wis.) in IMDM or in PRMI 1640 (50% v/v/ containing 5% dimethyl sulfoxide DMS, Baker Chemical Co., Phillipsburg, N.J.) is added over 1 minute with constant stirring by the tip of the pipette for 2 minutes. Two ml of warm IMDM (or RPMI 1640) are thereafter added over 2 minutes, followed by 7 ml IMDM over 3 minutes. The cell suspension is washed once (10 minutes, 23° C.) and then resuspended in 50 ml of IMDM. One ml of the cell suspension is dispensed out in a 24-well flat-bottom plate.

Normal spleen cells are taken from the spleen at a concentration of 10$^5$ cells per ml and used as feeder cells, and the plate(s) placed in a CO$^2$ incubator at 37° C. Half the supernate is removed, taking care not to disturb the cells. 1 ml IMDM is replaced with 85% IMDM, 15% FBS containing the hypoxanthine:aminopterin:thymidine (HAT medium). Then half the supernate is repalced and 1 ml HAT is added every second to third day until vigorous growth of hybrids is observed. Supernatant from each well is tested in HIV-1 ELISA (ENI) and on HIV-1 Ab Quick Western Blot for titer and for the presence of anti-gp 48, respectively, as well as gp 48 -related proteins.

The hybrid colonies showing anti-gp 48 activity are then cloned by limiting dilution within 2 weeks of fusion (Oi and Herzenberg). 1 ml of a well-mixed cell suspension is extracted from the well containing the antibody in question. Serial dilutions are made to achieve a final concentration of 10 cells/ml in RPMI 1640. 1 ml is seeded to each well in 24 well plates, which are filled with 10$^5$ feeder cells (normal splenic cells). The culture is closely monitored daily for the emergence of clones.

Culture wells containing single clones are noted by day 5 to 7 and tested at confluence. Hybrid clones are cloned 2 to 3 times to insure monoclonality.

EXAMPLE 9

Preparation of Antiiodiotype Pig/Human Monoclonal Antibody

A mini pig is immunized with HIV-1 containing gp 48 proteins in the same manner as described in Example 2 for a Yorkshire breed. The mini pig is then tested every 14 days (at each revaccination). When the titer of anti-gp 48 IgG is optimally high, the pig is then bled and the immunoglobulin is purified using the method described by Carter and Boyd (Carter, R. J. and N. D. Boyd, J. Immunol. Methods 26:213 (1979)). The immunoglobulin IgG is then administered s.c. in 200 ug portions to a Yorkshire pig, mixed with Freund complete adjuvant. After 14 days 200 ug of IgG is mixed with Freund's incomplete adjuvant and administered s.c. After another 14 days, 200 ug of IgG is mixed in saline and administered s.c. using methods described by Sacks, D. L. et al, J. Immunol. 135:4155 (1985) to form the antiidiotype antibody against anti-gp 48.

To ascertain the presence of the antiidiotype antibody, blood is withdrawn from the pig and dotted onto nitrocellulose paper at the following dilutions: undiluted, 1:10, 1:100, 1:1000. 1 ul of the immunoglobulin is dotted per dot. When dried, the dots are reacted with anti-gp 48-containing serum for humans. When a gp 48 positive dot is recognized, the pig is given a booster dose of about 200 ug s.c, and i.p., in the same manner as described in Example 8. 2–5 days after the booster, the pig is sacrificed and the spleen is removed and used for separation of immunocytes, The hybrid cell is obtained by using the human myeloma cell G 4672 B (NIGMS) to obtain a pig/human hybrid. The hybrid is then propagated and cloned. The clones are checked against anti-gp 48 by using the monoclonal antibody as a antiidiotype antibody or "gp 48 antigen". Either the dot for testing the gp 48 monoclonal for binding to anti-gp 48 sera, or monoclonal antibodies, may be used. Alternatively, ELISA systems can be used to titrate out the titer and follow development of the clones.

Example 10

HIV-1 Lympho-Test

The lympho-test is a diagnostic method for detecting the presence or absence of HIV-1 in a biological sample. An advantage of the lympho-test is that it allows reliable mass screening of many samples at a time. The method uses the gp 48 antibody which selectively binds to HIV-1 infected cells and does not bind to healthy non-HIV-1 infected lymphocytes. The binding of the antibody system can be detected using a sandwich immunoassay where the second antibody is an anti-human immunoglobulin, fluorescein isothiocyanate conjugated (anti-immuno-globulin-FITC). The labelled antibody can be detected using a Flow cytophotometer, such as an Ortho Flow cytophotometer or a simpler type of fluorescence measurement on a Pandex flourescence concentration analyzer (FCA-Pandex Laboratories, Inc.). The lympho-test can also be used to detect HTLV-1, HIV-2 and HTLV-1.

Blood was drawn from an individual in a yellow tube containing ACD. The whole blood was poured into a leukoPREP cell separation tube (Becton Dickinson) and subsequently centrifuged for a least 15 minutes at 1,500 to 1,800 G at room temperature. After centrifugation, the upper layer in the tube was plasma and the layer immediately on the gel in the tube was mononuclear cells including the lymphocytes. The remainder portion of the whole blood was located below the gel in the lower gradient. The plasma was removed using a Pasteur pipette and the mononuclear lymphocyte layer was removed into a tissue culture tube (Felton) 1 ml. of phosphate buffered saline (PBS) at a pH of 7.4 was added to the lymphocytes. The lymphocytes were transferred to another tube (alternatively at this point they could be transferred directly to a 96 well plate) and porcine anti-gp 48 was added to the tube at a dilution of 1:100 in PBS. The tubes were incubated at 4° C. for 30 minutes and subsequently the cells were washed twice for 10 minutes in PBS buffer. A second flourescein isothiocyanate conjugated (FITC) antibody was added (50 ul) at a dilution of 1:125 and the tubes were incubated at 4° C. for 30 minutes (alternatively this step can also be done in the 96 well plate). The cells were subsequently washed twice for 10 minutes in PBS. After the last wash the cells were resuspended in 100 ul of PBS and transferred to a 96 well plate. The FITC activity was then measured using a Pandex Flourescence concentration analyzer (FCA).

Equivalents

Those skilled in the art will know, or be able to ascertain, using no more than routine experimentation, many equivalents to the specific embodiments of the invention described herein.

These and all other equivalents are intended to be encompassed by the following claims.

I claim:

1. An isolated immunoglobulin product produced by immunizing a pig with a HIV viral lysate containing a gp48 antigen and isolating the immunoglobulin fraction which contains antibodies to the gp48 antigen wherein said immunoglobulin product has been selected for binding to gp48 antigen.

* * * * *